United States Patent [19]

Kocal et al.

[11] Patent Number: 4,634,801

[45] Date of Patent: Jan. 6, 1987

[54] MOTOR FUEL ALKYLATION PROCESS UTILIZING LOW ACID

[75] Inventors: Joseph A. Kocal, Gurnee; Tamotsu Imai, Mount Prospect, both of Ill.

[73] Assignee: UOP Inc., Des Plaines, Ill.

[21] Appl. No.: 791,289

[22] Filed: Oct. 25, 1985

Related U.S. Application Data

[63] Continuation-in-part of Ser. No. 764,707, Aug. 12, 1985.

[51] Int. Cl.$^4$ .......................... C07C 3/52; C07C 3/54
[52] U.S. Cl. .................................................... 585/724
[58] Field of Search ......................................... 585/724

[56] References Cited

U.S. PATENT DOCUMENTS 3,778,489 12/1973 Parker et al. ....................... 585/724

Primary Examiner—Curtis R. Davis
Attorney, Agent, or Firm—Thomas K. McBride; John F. Spears, Jr.

[57] ABSTRACT

A novel hydrocarbon alkylation catalyst is disclosed comprising a mineral acid and an ether component. A process for utilizing the novel catalyst is also disclosed.

4 Claims, No Drawings

MOTOR FUEL ALKYLATION PROCESS UTILIZING LOW ACID

CROSS-REFERENCE TO RELATED APPLICATION

This application is a continuation-in-part of prior copending application Ser. No. 764,707, filed Aug. 12, 1985, entitled Novel Motor Fuel Alkylation Catalyst and Process for the Use Thereof, the contents of which are incorporated by reference thereto.

BACKGROUND OF THE INVENTION

This invention relates to a process for the alkylation of an isoparaffin with an olefin acting agent. Additionally, the invention relates to a low acid alkylation process in which a novel catalyst is used to produce an alkylate having improved antiknock properties. Accordingly, the invention has particular utility in the production of high octane alkylate for use as a motor fuel blending component.

Alklation of isoparaffinic hydrocarbons, such as isobutane and isopentane, with olefinic hydrocarbons such as propylene, butylene and amylenes or with other olefin-acting agents such as $C_3$–$C_5$ alkyl halides, etc., using mineral acids such as hydrogen fluoride is well known as a commercially important method for producing gasoline boiling range hydrocarbons. The $C_5$–$C_{10}$ hydrocarbons typically produced in isoparaffin-olefin alkylation operations are termed "alkylate." Alkylate is particularly useful as a motor fuel blending stock. It possesses motor and research octane ratings high enough that it may be employed to improve overall octane ratings of available gasoline pools to provide motor fuels which comply with the requirements of modern automobile motors. High octane alkylate blending components are particularly important in producing motor fuels of sufficiently high octane when it is desired to avoid use of alkyl lead antiknock compounds in gasoline. A continuing goal in the art is to provide an economically attractive acid catalyzed alkylation process which provides an alkylate product having motor and research octane ratings which are higher than are attainable in conventional alkylation processes. This goal takes on special significance with the phaseout of alkyl lead antiknock compounds as blending agents for gasoline as mandated by government regulation.

In commercial isoparaffin-olefin alkylation operations using acid catalysts, generally, isobutane is the isoparaffin used and propylene, butylene and amylenes or a mixture of these olefins, are used as the olefin-acting agent. Typically the acid catalyst will comprise hydrogen fluoride. In conventional operations, the isoparaffin, olefin-acting agent and hydrogen fluoride catalyst are first contacted and thoroughly admixed in an alkylation reactor, forming a reaction mixture, or emulsion. After a relatively short time, the alkylation reaction is substantially complete and the reaction mixture is withdrawn from the alkylation reactor and is allowed to settle by gravity into immiscible hydrocarbon and catalyst phases in a settling vessel. The hydrogen fluoride catalyst phase thus separated is returned to the alkylation reactor for further catalytic use. The hydrocarbon phase separated in the settling operation is further processed, e.g., by fractionation, to recover an alkylate product and to separate unconsumed isoparaffin for recycle to the alkylation reactor. The recovered alkylate product may then be added to the motor fuel octane pool as a blending component. It is, therefore, desirable that the alkylate product has as high a research octane number as possible.

OBJECTS AND EMBODIMENTS

It is, therefore, an object of the present invention to provide an improved process for the alkylation of an isoparaffin with an olefin acting agent. An alternative object is to employ the improved process to produce an alkylate having good antiknock properties while minimizing the amount of acid utilized.

Accordingly, in one embodiment the present invention is a process for the alkylation of an isoparaffin with an olefin acting agent comprising contacting the isoparaffin with the olefin acting agent at alkylation conditions in the presence of a catalyst comprising an anhydrous, nonalcoholic mixture of from about 50 wt. % ether component wherein there is sufficient catalyst such that the molar ratio of mineral acid to olefin acting agent is less than about 25.

These as well as other objects and embodiments will become apparent upon review of the following more detailed description of the prior art and the invention.

INFORMATION DISCLOSURE

The art has recognized the use of acid catalyst modifiers in the process of alkylating an isoparaffin with an olefin. For example, U.S. Pat. No. 3,761,540 discloses that an isoparaffin may be alkylated with an olefin using hydrogen fluoride catalyst and a small proportion of $BF_3$. The $BF_3$ is disclosed as modifying the alkylation reaction in such a fashion as to minimize production of ethyl fluoride. The reference discloses that when the isoparaffin to olefin ratio in the reaction zone is less than about 4:1 a high octane value alkylate may be made by modifying the HF catalyst with $BF_3$ while minimizing alkyl fluoride formation.

U.S. Pat. No. 3,531,546 discloses the alkylation of organic compounds in the presence of a novel catalyst comprising a hydrogen fluoride-carbon dioxide complex. It is disclosed that by using the hydrogen fluoride-carbon dioxide complex a motor fuel alkylate having increased research octane number is thereby produced. The increased octane number results from improved isomer distribution in the alkylate.

A particular interest is U.S. Pat. No. 3,778,489. This reference discloses an alkylation process for alkylating alkanes with an alkene utilizing various strong acids including hydrofluoric acid in the presence of a catalyst promoter. At column 3, line 61 of the reference, it is disclosed that the preferred catalyst promoters contain either a hydroxy group such as alcohols or a hydroxy group precursor such as ethers *which cleave to form alcohols* under the acidic conditions of the subject invention. The most preferred compounds are disclosed to be the lower molecular weight alcohols such as ethyl alcohol, the lower molecular weight ethers such as diethyl ether and water. Accordingly, this reference discloses that ether compounds may be employed in the alkylation of alkanes and alkenes under conditions which promote the cleavage of the ethers to form alcohol. These ethers, therefore, do not act as catalyst in that they are not inert but rather cleave to form different compounds and are thereby consumed in the alkylation reaction. By way of distinction the present invention employs ether compounds as actual catalyst components, the conditions within the alkylation process being such to preserve the ether and inhibit any cleavage thereof to an alcohol.

In summary then the art has disclosed the use of catalyst promoters and in particular has disclosed the use of ether as a precursor of an alcoholic promoter. However, the art has not disclosed a catalyst comprising a strong acid such as hydrofluoric acid and an ether compound in which catalyst the ether is maintained as an ether as opposed to being cleaved to an alcohol. By means of the novel catalyst it is possible to reduce the amount of acid utilized in the alkylation of an isoparaffin and an olefin acting agent.

DETAILED DESCRIPTION OF THE INVENTION

To reiterate briefly the present invention relates to a process for the alkylation of an isoparaffin with an olefin acting agent comprising contacting the isoparaffin with the olefin acting agent at alkylation conditions in the presence of a catalyst comprising an anhydrous, nonalcoholic mixture of from about 50 wt. % ether component wherein there is sufficient catalyst such that the molar ratio of mineral acid to olefin acting agent is less than about 25.

As heretofore indicated the catalyst of the instant invention is for the alkylation of an isoparaffin with an olefin acting agent. Typical of the isoparaffins which may be utilized in the invention are isobutane, isopentane and similar isoparaffins. The preferred isoparaffins are isobutane and isopentane, particularly, isobutane. A mixture of two or more isoparaffins may also be employed, if desired. Conventional isobutane alkylation feedstocks are suitable for use in the present process. Such conventional isobutane feedstocks may contain some nonreactive hydrocarbons such as normal paraffins. For example, a conventional commercial isobutane alkylation feedstock generally contains about 95 wt. % isobutane, 4 wt. % normal butane and 1 wt. % propane.

Olefin-acting agents which are suitable for use in the process of the present invention include $C_3-C_6$ monoolefins, alkyl halides, or mixtures thereof. $C_3-C_5$ olefins are preferred. The process of the present invention may be applied to the alkylation of mixtures of two or more olefin acting agents with the same benefits and improvements as would be obtained in using a single olefin-acting agent. For example, many conventional olefin feedstocks utilized in commercial alkylation operation contain mixtures of propylene and butylenes, or propylene, butylenes and amylenes. Application of the present process to such olefin mixtures results in improvements in quality of the products obtained which are equal to the improvement obtained using a single olefin. Similarly, a mixture of $C_3-C_5$ alkyl halides and olefins in any proportion is also suitable in many cases, for example, when the halide is fluoride. The particularly preferred $C_3-C_5$ olefin feedstocks are conventionally derived from petroleum refining processes such as catalytic cracking and may contain substantial amounts of paraffins, lighter and heavier olefins, etc. Olefin feedstocks derived from such conventional sources are suitable for use in providing the olefin-acting compound used in the present process.

As heretofore indicated the catalyst used in the process of the present invention comprises an anhydrous, nonalcoholic mixture of mineral acid and ether component. It should be understood that by the term anhydrous it is meant that the water content of the acid should comprise no more than about 3 wt. % based on the total weight of the acid phase. The presence of water in the acid phase greatly increases the corrosive properties of the mineral acid, especially hydrofluoric acid, and results in the cleavage of the ether component to an alcohol. As will be more fully appreciated upon review of the appended examples substitution of an alcohol component for the ether component of the present invention yields inferior results. In this last respect it is a feature of the present invention that the catalyst be nonalcoholic. By nonalcoholic it is meant that the alcohol content of the acid phase be no more than about 3 wt. % on the weight of the acid phase.

Mineral acids which may be employed in the present invention comprise any mineral acid commonly used in alkylation processes. Such acids include sulfuric acid, halosulfuric acids such as fluorosulfuric acid or halogen acids such as hydrofluoric acid, etc. It is to be further understood that the term mineral acid is intended to encompass solid acid sources such as acidic resins or zeolites which are suitable for catalyzing the alkylation of an isoparaffin with an olefin acting agent. Especially preferred is the use of hydrofluoric acid.

Hydrofluoric acid is preferred because it is one of the most stable mineral acids. It can be subjected to high temperatures and pressures and to the action of other catalytic agents without being broken down. Many of its organic compounds decompose either by heat alone or in the presence of catalyst to regenerate hydrofluoric acid. This results in low catalyst consumption in the process. An important advantage of using hydrofluoric acid is that by virtue of its chemical stability and low freezing point, it may be employed over a wide range of operating conditions. Conditions may be employed which are most satisfactory thermodynamically or economically, without limitations due to catalyst properties. For example, in the alkylation reaction, ambient or slightly superambient temperatures may be used with hydrofluoric acid. Hence, it is unnecessary to utilize refrigeration as might be the case when certain other mineral acids are utilized as the alkylation catalysts. The vapor pressure of hydrofluoric acid makes it unnecessary to resort to extreme pressure to maintain the catalyst in liquid phase. Its freezing point permits its use at temperatures much lower than is possible with most catalysts which either freeze or become highly viscous at low temperatures. Although in the alkylation of isobutane with olefins to produce aviation blending fuel, the usual operating conditions are of the order of about 30° C., there are catalytic reactions which are favored by low temperatures. Since hydrofluoric acid catalyzes such reactions, it is a distinct advantage because of its physical properties. Conversely since hydrofluoric acid is thermally stable it can be employed at much higher temperatures than other alkylation catalysts. This is a unique property of hydrofluoric acid.

As heretofore indicated the catalyst of the present invention comprises from about 70 to about 95 wt. % mineral acid based on the weight of the acid catalyst. It is especially preferred that the invention comprise between about 85 and 95 wt. % mineral acid. This is especially true when the acid comprises hydrofluoric acid. A particularly preferred catalyst composition comprises about 90 wt. % hydrofluoric acid based on the weight of the acid phase.

A second feature of the present invention is an ether component. As heretofore indicated the art has been cognizant of utilizing ether as an additive for alkylation processes; however, in the prior art the ether was taught to be an alcohol precursor. Accordingly, the art is directed towards an alkylation process wherein an alcohol or alcohol precursors comprise a catalyst modifier. In contradistinction the present invention is directed toward a catalyst wherein the ether component is a true catalyst component in that the ether is not consumed in the reaction.

Any suitable ether may be utilized as the ether component. For example, the ether component may comprise lower molecular weight ether such as dimethyl ether, diethyl ether, dipropyl ether, etc. It is preferred, however, that the ether component comprises an ether that will be liquid at the conditions employed within the alkylation reaction zone. A particularly preferred ether component comprises methyl tert-butyl ether. Of course, it should be understood that the ether component may comprise a single ether species such as the preferred methyl tert-butyl ether, or the ether component may comprise a mixture of two or more ethers.

Alkylation conditions which may be employed in the process of the present invention include a temperature of from about 0° F. to about 200° F., a pressure sufficient to maintain the reactants and the catalyst in the liquid phase, and a contact time between the hydrocarbons and the catalyst of about 0.1 minute to about 30 minutes.

As heretofore indicated an object of the present invention is the production of a high octane alkylate by means of an acid catalyzed alkylation of an isoparaffin with an olefin acting agent wherein the process has lower acid requirements. It has been discovered that utilizing an alkylation catalyst comprising an anhydrous, nonalcoholic mixture of from about 50 to 99 wt. % mineral acid and from about 1 to about 50 wt. % ether component allows lower acid requirements than the prior art alkylation process while still maintaining the same octane properties of the alkylate. Accordingly, the amount of catalyst utilized in the present invention is sufficient such that the molar ratio of mineral acid to olefin acting agent is less than about 25. In contradistinction the prior art processes typically employ alkylation catalysts in an amount such that the molar ratio of mineral acid to olefin acting agent is 30 or more and as high as 50 or more. It is further preferred that the amount of catalyst employed in the present invention is such that the liquid volumetric ratio of mineral acid to isoparaffin and olefin acting agent is less than about 0.75 and preferably less than about 0.18. By way of distinction it should be noted that the amount of acid employed in the prior art processes is such that the volumetric ratio of acid to isoparaffin and olefin acting agent is generally 1.0 and commonly as high as 5.0 or more. As will be hereinafter demonstrated use of a novel catalyst allows the production of high quality alkylate with much lower acid use in the process. As will be readily apparent to one of ordinary skill in the art it is very desirable to minimize use of mineral acid in the alkylation process. For example as indicated heretofore a typical mineral acid employed in the alkylation process is hydrogen fluoride. The corrosive properties of HF acid are of course well known in the art. Use of HF as an alkylation catalyst therefore necessitates use of processing equipment employing exotic and expensive alloys such as monel, hastalloy, etc. By minimizing the HF requirements of a process it is contemplated that there will be a commensurate minimization of the use of such alloys. Moreover, as will be recognized by those of ordinary skill in the art it is advantageous to minimize the use of hazardous mineral acids such as HF.

In a particularly preferred embodiment, a reaction mixture of a catalyst comprising hydrogen fluoride and methyl tert-butyl ether, reactants and reaction products formed in the alkylation reactor is passed through a reaction soaker. In the description of the preferred embodiments herein provided it is intended that both the alkylation reactor and a reaction soaker, if one is utilized, are included within the scope of the term "alkylation reaction zone." Suitable reaction soakers are well known in the art. For example, the reaction soakers described in U.S. Pat. Nos. 3,560,587 and 3,607,970 may suitably be employed in the present process. Such reaction soakers are conventionally vessels equipped with perforated trays, baffle sections, of the like to maintain an alkylation reaction mixture in the form of a fairly homogeneous mixture, or emulsion, for a predetermined length of time. The alkylation reaction mixture of catalyst and hydrocarbons is maintained in the reaction soaker for a time which depends on the composition of the reaction mixture. Generally a reaction soaker residence time of about 1 minute to about 30 minutes is employed. The temperature and pressure maintained in the reaction soaker are substantially the same as the temperature and pressure maintained in the associated alkylation reactor.

Means for settling the reaction mixture effluent from the alkylation reaction zone in order to separate a settled hydrocarbon phase and an acid catalyst phase are well known in the alkylation art. Generally, the effluent alkylation reaction mixture recovered from an alkylation reaction or soaker comprises a mixture of unreacted isoparaffins, alkylation reaction products, acid catalyst, and catalyst-soluble organic materials, possibly with small amounts of light hydrocarbons, etc. When this alkylation reaction mixture is allowed to stand unstirred, i.e., settled, the alkylation reaction products, isoparaffins and light hydrocarbons form a lighter settled hydrocarbon phase. The acid catalyst phase comprising a mineral acid and ether component forms a separate phase. The settled hydrocarbon phase is then simply mechanically separated from the catalyst phase. The temperature and pressure maintained during such a settling operation are substantially the same as those described above in connection with the alkylation conditions employed in the reaction zone. The hydrocarbons and the catalyst are preferably in the liquid phase during the settling separation operation.

Some means for withdrawing heat from alkylation zone may be necessary for optimum operation of the process. A variety of means for accomplishing the heat withdrawal are well known. For example, the heat generated in the alkylation reaction may be withdrawn from the alkylation reactor by indirect heat exchange between cooling water and the reaction mixture in the reactor.

In order to demonstrate the benefits and advantages of the present invention in contrast to prior art alkylation methods the following example is offered. It is to be understood that the example is intended to be illustrative and in no way restrictive on the otherwise broad embodiments of the present invention as set forth in the claims appended hereto.

EXAMPLE I

This example was conducted in a pilot plant scale unit operation. The pilot plant comprised a monel autoclave in which the isoparaffin and olefin-acting agent are contacted with the acid catalyst. After sufficient time the hydrocarbon and acid phases were removed from the autoclave and passed to a settler in which the phases were allowed to separate. The acid phase was then removed from the settler and recycled back to the autoclave for contact with more hydrocarbon. The hydrocarbon phase comprising alkylate was removed from the settler and passed to neutralization facilities. Thereafter the hydrocarbon phase was collected for analysis.

In this example two different runs were made in the pilot plant. Both runs employed a catalyst comprising 90 wt. % hydrogen fluoride and 10 wt. % methyl tert-butyl ether. In both tests the conditions within the autoclave were a temperature of 20° C., a pressure of 130 psig, a hydrocarbon residence time of 25 minutes, and a stirring rate of 1800 rpm. However, in the first run the acid recycle pump was set to result in a volume ratio of acid phase to hydrocarbon phase (excluding the ether component of the catalyst) in the autoclave of 1.5. In the second run the acid recycle run was adjusted such that recycle rate was reduced to result in an acid phase to hydrocarbon phase (excluding the ether component of the catalyst) volumetric ratio of about 0.15. The HF to C$_4$-olefin molar ratio in the first and second run were 55.5 and 6.4, respectively. The mole ratio of isobutane to C$_4$ olefins was 7.9. The C$_4$ olefin distribution was 48.2% 2-butene, 23.2% 1-butene, and 28.6% isobutylene.

In each run the alkylate product was analyzed and the products were found to have the following compositions and research octane numbers.

| Run | First | Second |
|---|---|---|
| Molar Ratio of HF/HCBN: | 55.5 | 6.4 |
| Alkylate Composition: | | |
| $C_8^-$ | 6.4 wt. % | 5.9 wt. % |
| Trimethyl Pentane | 75.7 wt. % | 76.3 wt. % |
| Dimethyl Hexane | 12.0 wt. % | 11.8 wt. % |
| $C_8^+$ | 5.9 wt. % | 6.0 wt. % |
| Research Octane No.: | 96.4 | 96.5 |

As can be readily seen reducing the amount of acid present in the reaction zone by reducing the acid recycle rate resulted in substantially no change in product quality. Both runs yielded alkylate having the same high octane number and very similar isomer distribution. This unexpected and surprising result indicates that it is possible to achieve a high octane alkylate, while minimizing the acid requirements of the alkylation reaction zone by means of the invention.

What is claimed is:

1. A process for the alkylation of an isoparaffin with an olefin acting agent comprising contacting the isoparaffin with the olefin acting agent at alkylation conditions in the presence of a catalyst consisting essentially of an anhydrous, nonalcoholic mixture of from about 5 to 15 wt. % methyl tert-butyl ether and from 85 to 95 wt. % hydrofluoric acid wherein the volumetric ratio of hydrofluoric acid to isoparaffin and olefin acting agent is less than 0.75.

2. The process of claim 1 further characterized in that the isoparaffin comprises isobutane and the olefin acting agent comprises C$_4$ olefins.

3. The process of claim 1 further characterized in that the molar ratio of hydrofluoric acid to olefin acting agent is less than about 10.

4. The process of claim 1 further characterized in that the volumetric ratio is less than about 0.18.

* * * * *